United States Patent [19]

Yang

[11] Patent Number: 4,993,617
[45] Date of Patent: Feb. 19, 1991

[54] STRUCTURE OF HEAD SHIELD FOR WELDING PLIERS

[75] Inventor: Chin-Pou Yang, Changhua Hsien, Taiwan

[73] Assignee: Liso, Su-Land, Taipei, Taiwan

[21] Appl. No.: 436,012

[22] Filed: Nov. 13, 1989

[51] Int. Cl.⁵ ............................................. B23K 9/32
[52] U.S. Cl. ...................................... 228/57; 228/59; 2/11
[58] Field of Search .................. 228/57, 101, 59; 2/9, 2/11, 12, 15; 219/147

[56]  References Cited
U.S. PATENT DOCUMENTS 1,517,009 11/1924 Kniffen ..................................... 2/11
2,194,573 3/1940 Schulz ................................... 219/147
3,105,018 1/1938 Tatter .................................... 219/147
3,273,881 9/1966 Kiefer .................................... 228/57
4,785,954 11/1988 Li ......................................... 219/147

Primary Examiner—Sam Heinrich
Attorney, Agent, or Firm—Young & Forward

[57]  ABSTRACT

A welding apparatus that includes a welding rod pliers connected to a portable head shield by an elongated flexible articulated tube. The person can hold the pliers in one hand, with the flexible tube acting to position the shield in a proper location for viewing the weld connection. This feature leaves the person's other hand free to manipulate a clamp or other tool for holding the work pieces in place during the welding process.

5 Claims, 3 Drawing Sheets

STRUCTURE OF HEAD SHIELD FOR WELDING PLIERS

BACKGROUND OF THE INVENTION

In the field of arc welding with a welding rod and a portable head shield there is a problem, due to the fact that the person performing the welding operation must use one hand to hold the welding rod pliers and the other hand to hold the portable head shield. It is therefore impossible to position or maintain the work pieces (with a suitable tool) during the welding process.

SUMMARY OF THE INVENTION

The present invention provides a welding apparatus wherein a welding rod pliers is connected to a portable head shield by means of an elongated articulated tube, such that the head shield is effectively supported by the pliers. The person can thereby manipulate the pliers and head shield with one hand, leaving his other hand free for positioning the weldment.

The elongated articulated tube is transversely bendable in different directions so that the head shield can be shifted up, down, or to either side, for thereby effectively changing the sight line from the viewing window in the shield to the tip of the welding rod. The articulated tube is detachably connected to the welding pliers and the head shield so that the pliers and shield can be used in the conventional manner when desired, e.g. when it is not necessary to apply a holding force to the weldment.

THE DRAWINGS

FIG. 1-1 is an enlarged perspective view of a mechanical connection used between a hand grip and head shield in the FIG. 1 apparatus.

FIG. 1-2 is a perspective view of a cable-grip mechanism used in a pliers that forms part of the FIG. 1 apparatus.

FIG. 2 is a rear view of a head shield forming part of the FIG. 1 apparatus.

DESCRIPTION OF A PREFERRED EMBODIMENT OF THE INVENTION

Figure 2:
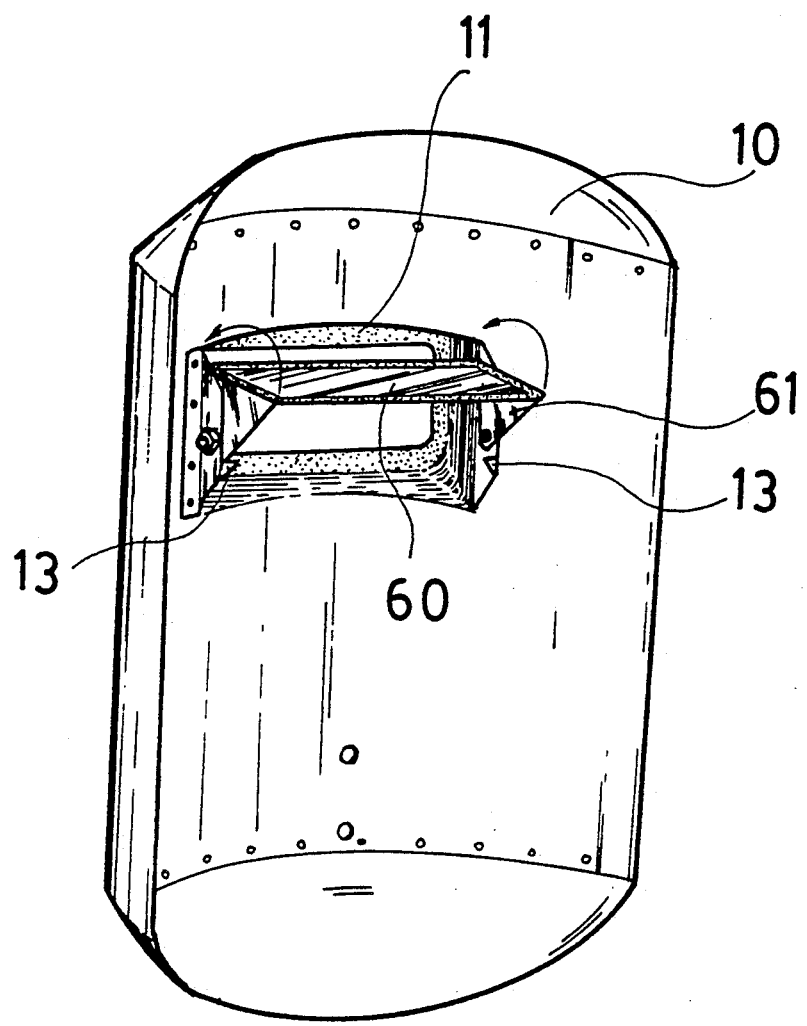

The drawings show a welding apparatus that comprises a protective head shield 10 having a viewing window 11 located in an upper portion of the shield, i.e. relatively close to the upper end of the shield body and relatively remote from the lower end of the shield body. Viewing window 11 includes a non-tinted transparent pane 12 and a darkly tinted pane 60. As shown in FIG. 2, pane 60 is a swingably (pivotably) mounted within the shield for movement to a swung-up position extending angularly away from pane 12. In its swung-up position, pane 60 can be cleaned of dust and contaminants. Pane 60 is swung down to a position behind, and parallel to, pane 12 prior to a welding operation (as in FIG. 3).

Welding operations are performed by a welding rod pliers 50 that includes an elongated handle, a pair of rod-gripper jaws at the upper end of the handle, and a swingable arm for operating the jaws. An electric cable 52 extends upwardly through the elongated handle to supply current to the jaws and to welding rod 70.

Pliers 50 is connected to shield 10 by means of an elongated flexible articulated tube 30. Each end of tube 30 has an end fitting that includes two parallel pins 31. A hollow block 20 is mounted on the front face of shield 10 below viewing window 11 to provide a detachable connection between the shield and one end of articulated tube 30. Socket openings 21 extend transversely through block 20 normal to the face of shield 10 to frictionally receive pins 31 on the tube 30 end fitting. The end fitting can be pulled away from block 20 when it is desired to separate tube 30 from shield 10.

Pliers 50 has socket openings 51 therein adapted to frictionally accept pins 31 on the left end of tube 30. The tube 30 can be separated from the pliers when it is desired to use the pliers and shield 10 in the conventional fashion, i.e. without tube 30.

Figure 3:
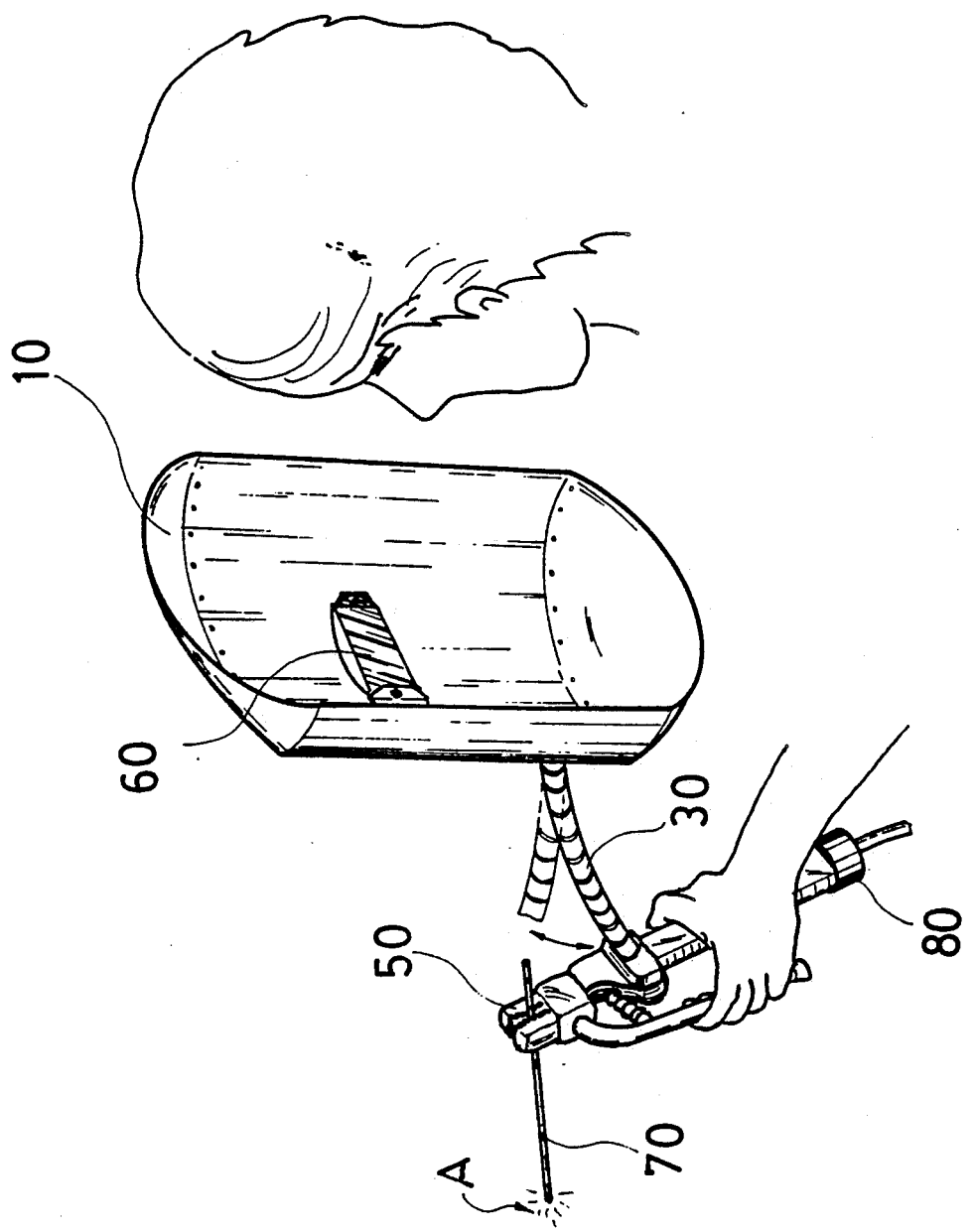
FIG. 3 is a perspective view of the FIG. 1 apparatus showing how it can be used during a welding operation.

FIG. 3 shows the apparatus when it is desired to support (suspend) shield 10 on tube 30 and the pliers. The person can look through viewing window 11 (dark pane 60) and observe welding rod 70 while holding pliers 50 to perform a welding operation. Shield 10 is supported entirely by tube 30 and pliers 50, thereby enabling the person's other hand to be used for holding a clamp or other tool for retaining the work in proper position. Tube 30 can be transversely bent in any desired direction to vary the location of shield 10 (or its angulation) relative to pliers 50, thereby changing the sight line from the viewing window 11 to the tip A of the welding rod, as might be necessary for different welding operations and different weld rod lengths.

As previously noted, tube 30 has detachable connections (at 31, 21 or 31, 51) with shield 10 and pliers 50. Shield 10 can be held in conventional fashion, used an elongated hand grip 40. A bifurcated end fitting 41 on the upper end of hand grip 40 is adapted to fit into a vertical slot extending upwardly within block 20. Ribs on the bifurcated end fitting 41 snap into transverse grooves 20 in the slot walls to frictionally retain hand grip 40 in a position where it can be used to manipulate shield 10.

Figure 1:
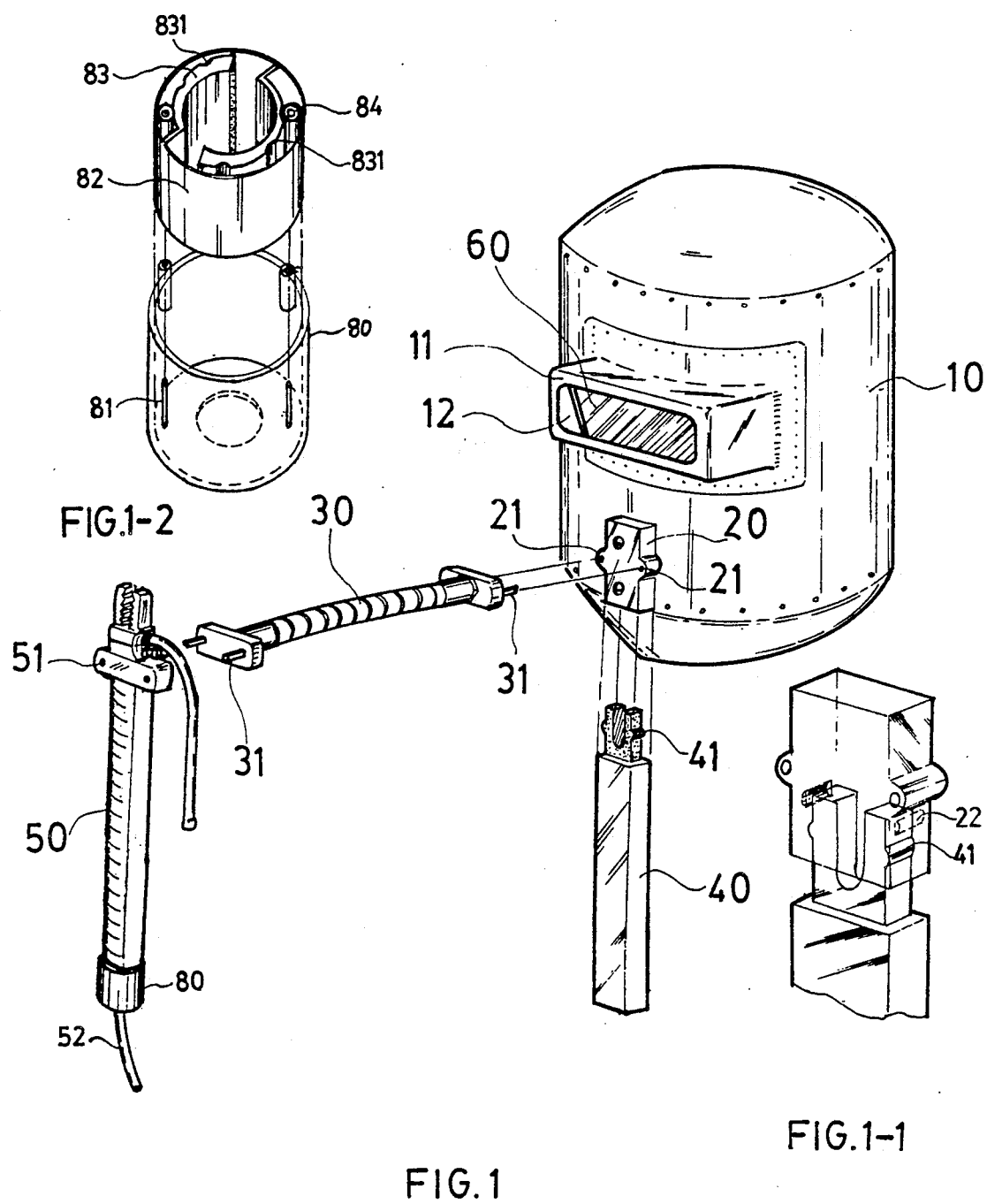
FIG. 1 is an exploded perspective view of an apparatus embodying the invention.

FIG. 1-2 shows a mechanism usable in the handle of pliers 50 to exert a gripping force on cable 52. The mechanism includes a rotary ring 80 having two internal pins 81 that act as support shafts for rollers 84. Two elactic cable-engagement members 83 are formed with a series of vertical grooves 831 in their outer faces. Manual rotation of ring 80 causes rollers 84 to ride along the surfaces of members 83 into the different grooves 831. Members 83 are eccentrically configured to have a variable radial thickness therealong, such that rollers 83 force members 83 to exert a gripping action on cables having different diameters. Ring 80 can be rotated to ensure that a given cable will be effectively clamped within the pliers handle, thereby minimizing stress at the cable-jaws connection that might otherwise loosen the cable and thus interfere with current flow.

With the apparatus shown in FIG. 3, the person is enabled to view the weld joint through viewing pane 60 (i.e. window 11) from different angles, depending on how tube 30 is articulatably adjusted. An ancillary advantage is that the full length of the welding rod can be used because the window can be oriented to achieve an effective sight line without interference from the pliers or other work pieces.

I claim:

1. A welding apparatus; comprising a protective portable head shield having an upper end and a lower end; a viewing window located in an upper portion of the shield;

an elongated flexible articulated tube; a first mechanical connection between one end of said articulated tube and said shield at a point on the shield located below the viewing window; a welding rod pliers having a pair of jaws adapted to grip a welding rod, and an elongated handle having means for thereon operating the jaws;

an electric cable extending through the cable to the jaws for supplying current to a welding rod while it is in the grip of the jaws; and a second mechanical connection between the handle and the other end of the flexible articulated tube; said articulated tube extending angularly away from the handle, such that the person operating the apparatus can look through the viewing window and observe the welding rod while holding the pliers to perform a welding operation; said head shield being supported entirely by the articulated tube and the pliers; said articulated tube being transversely bendable in a range of different directions for changing the sight line from the viewing window to the tip of the welding rod.

2. The welding apparatus of claim 1, wherein each mechanical connection is a detachable connection, whereby the flexible articulated tube can be separated from the pliers and the head shield.

3. The welding apparatus of claim 2, wherein said first mechanical connection comprises a block (20) mounted on the face of the head shield, a pair of socket openings extending through said block normal to the shield face, and a pair of pins (31) extending from said one end of the articulated tube for entry into the socket openings.

4. The welding apparatus of claim 3, and further comprising a hand grip (40) having a bifurcated end fitting (41); said block (20) having a vertical slot extending from its lower edge for receiving the bifurcated end fitting therein, whereby the hand grip can extend downwardly from the shield for shield manipulation purposes.

5. The welding apparatus of claim 1, wherein said viewing window comprises a transparent non-tinted pane, a darkly tinted transparent pane, and means for pivotally supporting said darkly tinted pane for movement between an operating position parallel to the non-tinted pane and a cleaning position swung away from the non-tinted pane.

* * * * *